United States Patent [19]

Mullin et al.

[11] Patent Number: 4,812,586

[45] Date of Patent: Mar. 14, 1989

[54] PREPARATION OF GROUP II METAL ALKYLS

[75] Inventors: John B. Mullin, Worcestershire, Great Britain; John C. Hamilton, Fife, Scotland; Elisabeth D. Orrell, Cheshire; Philip R. Jacobs, Merseyside, both of Great Britain; Deodattta V. Shenai-Khatkhate, Fife, Scotland

[73] Assignee: The Secretary of State for Defence in Her Britannic Majesty's Government of the United Kingdom of Great Britain and Northern Ireland, London, England

[21] Appl. No.: 948,348

[22] PCT Filed: Apr. 9, 1986

[86] PCT No.: PCT/GB86/00197

§ 371 Date: Jan. 27, 1987

§ 102(e) Date: Jan. 27, 1987

[87] PCT Pub. No.: WO86/06071

PCT Pub. Date: Oct. 23, 1986

[30] Foreign Application Priority Data

Apr. 9, 1985 [GB] United Kingdom ................. 8509055

[51] Int. Cl.$^4$ ............................ C07F 3/06; C07F 3/08

[52] U.S. Cl. .................................. 556/129; 544/225; 546/2; 546/12; 556/128

[58] Field of Search .......................................... 556/129

[56] References Cited

FOREIGN PATENT DOCUMENTS 80844 6/1983 European Pat. Off. .

OTHER PUBLICATIONS

Coates, J. Chem. Soc., pp. 3340–3348 (1962).

*Primary Examiner*—Michael L. Shippen
*Attorney, Agent, or Firm*—Nixon & Vanderhye

[57] ABSTRACT

A method of preparing high purity dimethyl cadmium or dimethyl zinc suitable for use in the deposition of Group II–VI epitaxial layers, which consists of forming an adduct of the metal alkyl with a non-chelating tertiary amine containing at least two tertiary amino groups per amine molecule, and subsequently dissociating the adduct to liberate the metal alkyl as a vapor. The adducts formed during the preparative method are found to dissociate readily on heating and yet are substantially involatile and so do not contaminate the liberated metal alkyl. A preferred amine suitable for use in the preparative method is 4,4' bipyridyl.

15 Claims, No Drawings

PREPARATION OF GROUP II METAL ALKYLS

The present invention relates to the preparation of Group II metal alkyls, especially in a high purity form.

Epitaxial layers of metals either in elemental form or contained in semiconductor compounds are being increasingly used in the electronics industry. Elements such as cadmium, zinc, gallium and indium may for example be deposited on substrate from their respective di- or tri-alkyls by thermal decomposition of the alkyls in the vapour phase to give the required epitaxial layers.

It is well-known that the presence of impurities in epitaxial layers can have a profound effect on the electrical properties of such layers. Generally speaking it is therefore very desirable to use in the epitaxial deposition process metal alkyls of the highest purity (although controlled impurities such as those provided by p- or n-type dopants may be intentionally added).

A method for the purification of dimethylcadmium has been disclosed by G. B. Coates et al, J Chem Soc, 1962, 3340. In this method an adduct of the alkyl is formed with 2, 2'-bipyridyl. This adduct can be purified by recrystallisation and dimethylcadmium can be liberated fairly rapidly from it in vacuo at about 70° C. One disadantage of this method is that the dimethylcadmium so produce is sometimes contaminated with significant amounts of 2, 2'-bipyridyl. This is particularly the case if higher temperatures are used for recovering the dimethylcadmium. since 2, 2'-bipyridyl contains the group V atom nitrogen, contamination of the dimethylcadmium in this way may have particularly serious consequences for semiconductors grown from this material since group V elements can act as p- type dopants.

The present invention seeks to overcome the above disadvantage by providing in a first aspect, a method of preparing a metal alkyl of geeeral formula $MR^1R^2$ in which M is selected from cadimum and zinc and $R^1$ and $R^2$ are independently selected from $C_1$-$C_8$ alkyl, which comprises the steps of:

(a) forming an adduct of the metal with a Lewis base comprising a tertiary amine aving at least two tertiary amino groups per molecule whose nitrogen atoms are capable of co-ordinating with M, and (b) dissociating the adduct to liberate the metal alkyl at a pressure P and at a temperature below the sublimation temperature or boiling point of the tertiary amine at pressure P as the case may be, wherein the tertiary amine has a molecular structure whose nitrogen atoms, for geometric reasons, co-ordinate with different atoms M such that the adduct formed has a vapour pressure of less than 1.33 Pa at its dissociation temperature at that pressure.

Preferably the vapour pressure of the adduct is less than 1.33 Pa at 20° C., most preferably at 3° C., above the dissociation temperature of the adduct at that pressure.

$R_1$ and $R_2$ are preferably independently selected from ethyl and methyl, and are most preferably methyl since dimethyl cadmium and dimethyl zinc are generally considered to be the most useful alkyls of these metals in subsequent processes for the deposition of roup II-VI epitaxial layers.

The dissociation temperature of the adduct may be measured by conventional thermogram techniques at a pressure of 1.33 Pa ($10^{-2}$ torr), by increasing the temperature of the adduct at a steady rate (e.g. 10° C. per minute) and recording the temperature at which a sharp increase in the heat generated by the adduct begins to take place, signalling the beginning of dissociation. The term "vapour pressure of the adduct" refers to the adduct itself and not its products of dissociation, and its volatility may be determined for the purpose of this invention by increasing the temperature of the adduct to its dissociation temperature at 1.33 Pa and observing whether it sublimes (if it is a sold at that temperature) or boiis (if it is a liquid at that temperature). If neither boiling nor sublimation is observed, then the adduct will in accordance with the method of the present invention have a vapour pressure of less than 1.33 Pa ($10^{-2}$ torr) at its dissociation temperature at that pressure. Similarly, the procedure may be repeated at 1.33 Pa at 20° C. or 30° C. above the dissociation temperature of tho adduct at that pressure.

The tertiary amine which is selected for use in the present method is a non-chelating amine, that is to say an amine whose molecules will not form a chelate structure with single $MR^1R^2$ atoms. The diamine 2,2'-bipyridyl is found to act as a Lewis base which forms a 1:1 mole adduct with diethylcadmium in which the nitrogen atoms of the diamine chelate the same cadmium atom as a bidentate ligand. The adduct which is formed by the present method does not have a chelate structure, that is to say no two nitrogen aroms within the amine molecule are capable of chelating the same metal atom M as a bidentate ligand. This may be confirmed by X-ray analysis of the crystalline structure of the adduct. The inventors have found that the effect of employing a non-chelating rather than a chelating amine is that the adducts formed using the former amines are substantially involatile at the typical temperatures and pressure required for their dissociation. As a result, the metal alkyl product is less likely to be contaminated with the adduct or the amine, especially if the amine itself is of low volatility and the alkyl is liberated as a gaseous product.

In terms of the structure of the non-chelating amine, this will usually mean that either at least one of the nitrogen atoms forms part of a hererocyclic ring structure or adjacent nitrogen atoms in the amine molecule are joined by a group which includes one or more aryl or alicyclic groups connecting between the nitrogen atoms. Preferably, the amine molecule will be free of any other atom capable of donating electrons to the atom M—on particular, the amine is preferably free of any other group V or VI atoms within its molecular strucrure. For this reason the amine is most preferably composed solely of the atoms nitrogen, carbon, and hydrogen.

Since the metal arom M will tend to form dative bonds with 2 nitrogen atoms and yet can only do so with one nitrogen atom on each tertiary amine molecule, each M will tend to bond with nitrogen atoms from separate amine molecules. Thus, the adduct may tend to form with an oligomeric or polymeric structure which will be long-chain containing alternate amine and alkyl molecules in the case of a diamine and cross-linked in the case of an amine having three or more tertiary amino groups per molecule. The main advantage of the possible formation of an oligomeric or polymeric adduct is that the adduct will be essentially involatile both below and at its dissociation temperature, so that it will be safe to handle and will not contaminate the liberated alkyl.

The metal alkyl may be separated by simple distillation, e.g. by heating the adduct by an oil bath, and collecting the distilled alkyl in a cold trap, or by fractionation, depending on the volatility of the amine. Preferably, separation is possible by simple distillation.

The required adduct specified above may be produced directly or indirectly, i.e. by direct reaction of the metal alkyl and the amine specified or by the formation of another known (precursor) adduct, e.g. of the metal alkyl with a volatile solvent such as diethyl ether, and then conversion into the required adduct by radical exchange upon addition of the amine. In either case the impure metal alkyl or the precursor adduct may be prepared by a known method. For example, the precursor adduct dimethylcadmiumdiethyl etherate may be prepared by the known method of reacting a cadmium dihalide, e.g. dichloride, with a methyl Grignard reagent, e.g. CH₃MgI in diethyl ether.

The method of the present invention is preferably carried out below atmospheric pressure, conveniently below 133 Pa (1 torr), so that the alkyl is released at low temperatures as a gaseous product and so is easily separated from the adduct.

The tertiary amine is preferably a low volatility solid having a melting point of between 50° and 200° C. and a boiling point of at least 200° C. at atmospheric pressure, and is preferably a solid at the dissociation temperature of the adduct at 1.33 Pa. More preferably, the melting point of the amine is at least 20° C., most preferably at least 30° C., above the dissociation temperature of the adduct at 1.33 Pa. In using such preferred amines, the risks of contaminating the metal alkyl product with amine are reduced to a minimum where the alkyl is liberated as a vapour.

Conveniently, the dissociation temperature of the adduct lies between 20° C. and 120° C. at 1.33 Pa. The adduct will not therefore dissociate at roo temperature (15° C.). At temperatures above 120° C., there is an increased danger that the metal alkyl will decompose explosively.

The tertiary amine which is used in the method of the present invention may fall into one of several classes of amine.

The amine may, for example, be of general formula I:

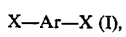

X—Ar—X (I), wherein each X is independently selected from tertiary amino substituent groups and Ar is an arylene bridging group, provided that the amino substituent groups X are separated by at least two arylene ring atoms on the Lewis ase molecule. Within the class, the amine is preferably of general formula II

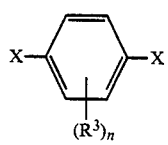

wherein X is as defined above, n is 0 or an integer from 1 to 4, and each $R^3$ is independently selected from $C_1$–$C_8$ alkyl. More preferably, X is $NR^4R^5$ where $R^4$ is $C_1$–$C_8$ alkyl and $R^5$ is $C_1$–$C_8$ alkyl or

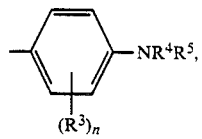

provided that the number of nitrogen atoms in the group X is from 1 to 3. Most preferably, $R^4$ and $R^5$ are independently selected from $C_1$–$C_8$ alkyl and n 0s o. An example of this most preferred type of amine is N,N,N',N'- tetramethyl-p-phenylene diamine.

Alternatively, the tertiary amino may comprise a pyridyl compound substituted in the meta-ring position or, preferably, the para-ring position by a tertiary amino group. The compound is preferably substituted in the para-ring position by X where X is —$NR^4R^5$ as defined above, and may be, for example, 4-dimethylamino-pyridine. More preferably, however, the pyridyl compound is of general formula III

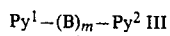

$Py^1$—$(B)_m$—$Py^2$ III wherein $Py^1$ and $Py^2$ are independently selected from optionally-substituted pyridyl provided that at least one of $Py^1$ and $Py^2$ is either optionally-substituted 3-pyridyl or optionally-substituted 4-pyridyl, B is arylene, alkylene or cycloalkylene, and m is 0 or 1. Examples of suitable compounds of general formula III are 3,3'-bipyridyl and, most preferably, 4,4'-bipyridyl . 4,4'-bipyridyl is especially preferred because when it forms an adduct with dimethyl cadmium the dissociation temperature of the adduct at 1.33 Pa is found to be some 20° C. below the melting point of the amine.

As a yet further alternative, the tertiary amine may be an optionally-substituted pyrazine, preferably one of general formula IV

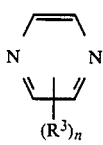

IV wherein $R^3$ and n are as defined above.

According to a second aspect of the present invention, there is provided an adduct which is the product of step (a) of the method according to the first aspect.

It has been discovered that the non-chelating tertiary amines used in the present method are especially suitable for use in obtaining alkyls of formula $MR^1R^2$ in purified form. The adducts formed between those metal alkyls and these amines are, generally speaking, solids at room temperature (20° C.) which may, prior to separation of the metal alkyl by distillation, be subjected to one or more of the techniques suitable for the purification of solids, e.g. crystallisation from solution and zone refining.

It has been discovered that use of these non-chelating amines in the production of alkyls of formula $MR^1R^2$ in high purity form is unexpectedly superior to the use of chelating analogues. It is beleived that this is because the non-chelating amines form an oligomer or a polymer complex structure from which the metal alkyl molecule may be more easily dissociated upon decomposition. For example, as described below, dimethyl cadmium may be separated more easily by simple distillation from the adduct it forms with the non-chelating 4,4'-bipyridyl than from the adduct it forms with the chelating 2, 2'-bipyridyl.

According to a further aspect of the present invention, therefore, there is provided an adduct of a metal alkyl of formula $MR^1R^2$ with a Lewis base comprising a tertiary amine, in which M is cadmium or zinc, $R^1$ and $R^2$ are independently selected from $C_1$–$C_8$ alkyl, and the tertiary amine has at least two tertiary amino groups per molecule whose nitrogen atoms are capable of co-ordinating with M, wherein the adduct contains at least two molecules of the tertiary amine per molecule of the adduct.

Where the Lewis base is a tertiary diamine, the adduct will generally be of formula $(MR^1R^2)_x \cdot L_y$ where L is the Lewis base, x and y are integers, y is at least 2, and x is from (y−1) to (y+1). The adduct may be in the form of a copolymer of the diamine and the metal alkyl which has an oligomeric or polymeric backbone containing at least two repeat units of formula $-(MR^1R^2)-$.

The purified metal alkyl produced by the method of the present invention may be used in a known way particularly for the deposition on a substrate of cadmium or zinc epitaxial layers either in single elemental form or as binary or multi-elemental II-VI compound layers by co-deposition with other suitable elements such as tellurium (e.g. as diethyl telluride) and mercury (e.g. from mercury vapour) which together with cadmium give cadmium mercury telluride. Essentially the cadmium or zinc is deposited from the cadmium or zinc alkyl by transporting the alkyl as a gas to a reaction vessel containing the substrate and thermally decomposing the alkyl in the vessel. Controlled impurities, e.g. n-or p-type dopants such as gallium or arsenic, may be co-deposited by adding trace amounts of the alkyls of these elements to the stream of gas or gases to be thermally decomposed. Examples of methods of the use of cadmium alkyls to deposit cadmium epitaxially by thermal decomposition are described for example in UK patent specification No. 2078695A the subject matter of which specification is incorporated herein by reference.

Examples of the method of the present invention and examples of comparative methods will now be described.

All solvents were carefully dried by distillation from sodium diphenylketyl and were degassed prior to use. Reactions were carried out in an atmosphere of "white spot" nitrogen purified by passed over a column consisting of $Cr^{2+}$ on silica. All greaseless joints and taps were employed and manipulations were carried out using standard schlenk line and catheter tubing techniques.

All Lewis bases were reagent grade and were purified by crystallisation from an ethereal solution such as diethyl ethor, or sublimation in vacuo (1.33 Pa).

Microanalyses (C,H, and N) were recorded on a Carlo-Erba 1106 carbon, hydrogen and nitrogen analyser. $^{113}Cd$ and $^{125}Te$ n.m.r. spectra were recorded on a Bruker Associates WM250 nuclear magnetic resonance spectrometer operating in the Fourier Transform mode with noise proton decoupling and $^1H$ n.m.r. spectra on a Perkin Elmer R12B spectrometer and a Bruker Associates WP-80 nuclear magnetic resonance spectrometer. Mass spectra were recorded on the Associated Electrical Industries Ms902 double focussing mass spectrometer. Trhermograms were measured on a Perkin Elmer DSC 2. Differential Scanning Calorimeter with a heating rate of 10° C. min.$^{-1}$ Melting points were determined on an electrothermal melting point apparatus in closed capillaries under argon and are uncorrected.

Example 1 (comparative)

Preparation of impure dimethylcadmium $Me_2Cd$

MeI (310 cm$^3$) was slowly added to Mg (115 g) in diethyl ether (870 cm$^3$) over 11 hrs. The Grignard reagent produced was added to $CdCl_2$ (215 g) in diethyl ether (502cm$^3$) over 90 hrs at a temperature between 45° and 55° C.

The diethyl ether/$Me_2Cd$ mixture was distilled at 35°–85° C. over 6 hrs (1st fraction) and then at 100° C. over 4 hrs (2nd fraction) and at 120°–123° C. for 4 hrs (3rd fraction). 2,2'-bipyridyl (125 g) was added to the 1st fraction and then the 2nd and 3rd fractions were added. Diethyl ether was removed at room temperature to give yellow crystals (2,2'-bipyridyl-dimethylcadmium adduct) from which dimethylcadmium was distilled at 80°–95° C. under reduced pressure (1.33 Pa). The yield was 123 g (75%). The dimethyl cadmium collected in a cold trap was contaminated by the undissociated adduct which gave it a yellow colouration, indicating that the adduct had a boiling/sublimation point at 1.33 Pa of about 80° C. Differential scanning calorimetry and electrothermal srudies shomed that the adduct began to dissociate at 67° C. (at 1.33 Pa) and melted at about 75° C.

EXAMPLE 2

N,N,N',N', -tetramethyl-p-phenylene diamine, TMPD (4.92 g) was added to $Me_2Cd$ produced as in Example 1 above in diethyl ether (25 cm$^3$). The other was evaporated from the resulting dark brown solution and benzene was added to the residue until it dissolved. A few drops of petroleum ether were added until crystals re-appeared. The petroleum ether and benzene were removed by filtration. Further dissolution of the crystals in petroleum ether followed by cooling to about 5° C. yielded high purity crystals of the adduct of $Me_2Cd$ with TMPD. Nuclear magnetic resonance $^1H$ (NMR) and microanalysis studies revealed that the adduct contained $Me_2Cd$ and TMPD in the molar ratio 2:3 indicating the linking of two or more molecules of TMPD with molecules of $Me_2Cd$ in a linear arrangement such as TMPD-$Me_2Cd$-TMPD-$Me_2Cd$-TMPD.

The adduct of $Me_2Cd$ and TMPD was then heated at about 80° C. in vacuo ($10^{31 2}$ torr, 1.33 Pa) to yield high purity dimethyl cadmium which was collected in a cold trap. Differential scanning calorimetry and electrothermal studies showed that the adduct melted at about 35° C. and began to dissociate (at 1.33 Pa) at about 33° C.

EXAMPLE 3

Impure dimethyl cadmium, $Me_2Cd$, was produced as in Example 1 above. 4,4'-bipyridyl (bipy) (2.35 g) was then added to the $Me_2Cd$ (2.11 g) in tetrahydrofuran. The solution was then cooled to about 5° C. Crsytals were removed from the solution and washed in petroleum ether. $^1H$ nmr and microanalysis revealed that the adduct contained $Me_2Cd$ and bipy in the molar ratio 1:1 indicating the linking of two or more molecules of bipy by the same number of molecules of $Me_2Cd$ either in a linear arrangement such as by-$Me_2Cd$-biPy-$Me_2Cd$ or a cyclic arrangement such as

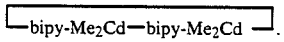.

The adduct of Me₂Cd and bipy was then heated at about 110° C. in vacuo (10⁻² torr, 1.33 Pa) to yield high purity dimethyl cadmium which was collected in a cold trap. Differential scanning calorimetry and electrothermal studies showed that the adduct melted at about 138° C. an began to dissociate (at 1.33 Pa) at about 83° C.

EXAMPLE 4

Dimethylcadmium (9 g, 6.32×10⁻² gmoles) was added in vacuo to a solution of 4-dimethylaminopyridine (6.14 g, 5.03×10⁻² gmoles) in tetrahydrofuran (50 cm³). The frozen contents were warmed to room temperature to dissolve any crystalline solid and then the adduct crystals were brought out of solution by cooling to −30° C. overnight. The solvent and excess dimethylcadmium were filtered off under nitrogen, first of all at 0° C. and then at room temperature, until the crystals were dry. This produced a very pale brown crystalline solid.

¹H Nuclear magnetic resonance and microanalysis studies revealed that the adduct contained Me₂Cd and dimemethylaminopyridine in the molar ratio 1:1.

The adduct of Me₂Cd and 4-dimethylaminopyridine was then heated to 65° C. at 1.33 Pa, 5° C. above its dissociation temPerature at that pressure, to yield pure dimethylcadmium, below the melting point of the adduct, which was collected in a cold trap maintained at a liquid nitrogen temperature. sublimation and melting was found to occur at and above 70° C. (Yield of dimethylcadmium=57%).

EXAMPLE 5

Dimethyl Cadmium (6.27 g, 4.40×10⁻² gmoles) was added in vacuo to a solution of 3,3'-bipyridyl (5 g, 3.20×10⁻² gmoles) in diethyl ether (60 cm³). The frozen contents of the reaction mixture were then warmed up to room temperature to dissolve the crystalline solid present. The adduct crystals were brought out of solution by leaving at −30 ° C. overnight. The diethyl ether and excess dimethylcadmium were filtered off under nitrogen, first of all ° at 0° C. and then at room temperature, until dry, producing a pale brown crystalline solid.

¹H Nuclear magnetic resonance revealed that the adduct contained Me₂Cd and 3,3'-bipyridyl in the molar ratio 1:1.

The adduct of Me₂Cd and 3,3'-bipyridyl was then heated to 75° C. in vacuo (1.33 Pa) to yield pure dimethylcadmium which was collected in a cold trap maintained at liquid nitrogen temperature. No sublimation of adduct was found to occur up to 80° C. Me₂Cd yield: 40%.

Dimethylzinc used in the following Examples 6–8 was prepared by the reaction of Grignard intermediate, methylmagnesium iodide and zinc chloride in a high boiling point ether (e.g. isoamylether or isopentyl ether) as outlined below:

(a) Preparation of MeMgI in Isoamylether

Iodomethane (78 cm³, 1.25 gmole) was added dropwise over a period of 4 hours under the atmosphere of dry nitrogen to a suspension of magnesium turnings (32 g,1.32 g atoms) in isoamyl ether 500cm³) containing traces of 1,2 dibromoethane (2 cm³) as an initiator. The reaction mixture was heated under reflux on a water bath maintained ° at 45° C. for 6 hours after the complete addition of iodomethane. The reaction mixture was then evacuated at room temperature in order to remove unreacted iodomethane (if present).

(b) Preparation of Dimethylzinc

MeMgI solution in isoamylether prepared as in (a) was added dropwise to the suspension of dry zinc chloride (71.44 g) 0.52 gmole) in isoamyl ether (50cm³), under an atmosphere of dry nitrogen, over a period of 5 hours in a three-necked-flask equipped with a mechanical stirrer, a vigreux column, and a reflux condenser. After the complete addition of MeMgI, the reaction mixture was refluxed over a water bath, maintained at 60° C. for 8 hours.

Dimethylzinc was obtained by the distillation of reaction mixture at atmospheric pressure on a wax bath maintained at 180° C. (° 42.512° g, Yield=85%, B.pt of collected fraction 45°-46° C.)

EXAMPLE 6

Dimethylzinc (2.73 g, 2.862×10⁻² gmole) was distilled in vacuo into a solution of 4,4'-bipyridyl (2.41 g, 1.537×10⁻² gmole) in diethylether (100 cm³). A pale yellow microcrystalline precipitate was obtained when the contents of the reaction mixture were warmed to room temperature. The ether and excess dimethylzinc were removed by filtration under a nitrogen atmosphere and by successive washings with diethyl ether cooled to 4° C. The adduct obtained was dissolved in dry tetrahydrofuran (40 cm³) and the resulting solution was concentrated to half its volume by removal of tetrahydrofuran in vacuo. Pure crystals of adduct were obtained by cooling the concentrated solution to −30° C. overnight.

¹H Nuclear magnetic resonance and microanalysis studies revealed that the adduct contained Me₂Zn and 4,4'-bipyridyl in the molar ratio 1:1.

The adduct of Me²Zn and 4,4'-bipyridyl was then heated in vacuo (1.33 Pa) to 90° C. to yield pure dimethylzinc which was collected in vacuo in a cold trap. The dissociation of adduct was found to occur between 85°–90° C. No sublimation of adduct was found to occur upto 90° C. (Yield of dimethylzinc=68%).

Example 7

Dimethylzinc (2.02 g, 2.12×10² gmoles) was added in vacuo to a solution of 3,3'-bipyridyl (3.29 g, 2.10×10⁻² gmoles) in diethyl ether (20 cm³). The frozen contents of the reaction mixture were then warmed to room temperature to obtain a pale yellow microcrystalline precipitate. The ether and excess dimethylzinc were removed by filtration under a nitrogen atmosphere and by successive washings with diethyl ether cooled to 4° C. The adduct obtained was dissolved in dry tetrahydrofuran (50 cm³) and resulting solution was concentrated to half its volume by removal of tetrahydrofuran in vacuo. Pure crystals of adduct were obtained by cooling the concentrated solution to −30° C. overnight.

¹H Nuclear magnetic resonance and microanalysis studies revealed that the adduct contained Me₂Zn and 3,3'-bipyridyl in the molar ratio 1:1.

The adduct of Me₂Zn and 3,3'-bipyridyl was then heated to 90° C. in vacuo (1.33 Pa) to yield pure dimethylzinc which was collected in a cold trap maintained at a liquid nitrogen temperature. No sublimation of adduct was found to occur up to 90° C.. (yield of dimethylzinc=98%).

EXAMPLE 8

Dimethylzinc (3.61 g, 3.77×10² gmoles) was added in vacuo to a solution of 4-dimethylaminopyridine(3.24 g, 2.65×10⁻² gmoles) in diethylether (200 cm³). The frozen contents of the reaction mixture were then warmed to obtain a clear colourless solution which was stirred at room temperature for 30 minutes and then was subjected to concentration by the removal of diethyl ether and excess dimethylzinc in vacuo. Pure crystals were obtained by cooling the concentrated solution (volume=50 cm³) to −30° C. overnight.

¹H Nuclear magnetic resonance and microanalysis studies revealed that the adduct contained Me₂Zn and 4-dimethylaminopyridine in the molar ratio 1:1.

The adduct of Me₂Zn and 4-dimethylaminopyridine was then heated to 80° C. in vacuo (1.33 Pa) to yield pure dimethylzinc which was collected in a cold trap maintained at a liquid nitrogen temperature. The dissociation of adduct was found to occur between 75°–80° C. whereas the sublimation of adduct was observed at temperatures between 100°–110° C.

COMPARATIVE EXAMPLE 9

1,4 Dioxan (2.36 cm³) was added to dimethyl cadmium (3.7 g) in diethyl ether. The ether was removed by evacuation to leave a white crystalline solid (4.3 g).

¹H nmr studies revealed a 1:1 adduct of 1,4 dioxan and dimethyl cadmium. The yield was 75%.

The adduct melted at 57° C. he adduct sublimed but did not give off Me₂Cd on heating at reduced pressure. The adduct is known to be a chelate structure.

COMPARATIVE EXAMPLE 10

Ethylene diamine (1.1 cm³) was added to dimethyl cadmium (2.92 g) in diethyl ether (15 cm⁵).

The mixture was stirred at room temperature. A reaction occurred causing the emission of gas resulting in the solution turning green/brown. The ether was removed by evacuation and a green/brown slurry was recovered. This was left overnight in a fume cupboard. It emitted more gas resulting in a dark green dry solid. Mass spectral analysis of the green solid showed no sign of Me₂Cd or indeed of any cadmium at all.

The conclusion reached was that the protons on the ethylene diamine are too acidic and result in the breakdown of Me₂Cd.

COMPARATIVE EXAMPLE 11

Tetramethyl ethylene diamine (TMED) was added to Me₂Cd (2.85 g) in diethyl ether 10 cm³). The ether was pumped off to reveal a yellow crystalline solid. On heating under reduced pressure the crystals sublimed to produce a white solid at 70° C. ¹H nmr studies and microanalysis showed the compound to contain Me₂Cd and TMED in a 1:1 rtio. Microanalysis confirmed the result. Differential Scanning Calorimetry revealed the adduct to have a melting point of 62° C. and a sublimation temperature at 1.33 Pa of 70° C.

Dimethyl cadmium could not be dissociated from the adduct because of the chelate structure formed.

COMPARATIVE EXAMPLE 12

Triphenylamine (TPA) (6.54 g) was added to Me₂Cd (1.86 g) in petroleum ether (30 cm³). The resulting slurry was cooled to about 5° C. No crystals were isolated. The petroleum ether was removed by pumping and toluene was added. The TPA dissolved in the toluene when placed in a refrigerator yielded white crystals. ¹H nmr analysis showed them to be TPA (no Me₂Cd). A study of shifts in tetrahydrofuran showed no sign of coordination between the TPA and Me₂Cd.

COMPARATIVE EXAMPLE 13

Dimethylanaline (DMA) (9 cm³) was added to Me₂Cd (5.5 g) in diethyl ether. The mixture produced no heat and no precipitation was observed. The solution was placed in a refirgerator. No crystals were produced.

The chemical shifts of the components were observed by ¹H nmr to see whether any changes had taken place. None were indicated.

We claim:

1. A method of preparing a metal alkyl of general formula MR¹R², in which M :s selected from cadmium and zinc and R¹ and R² are independently selected from C₁–C₈ alkyl. which comprises the steps of
   (a) forming an adduct of the metal alkyl with a Lewis base comprising a tertiary amine having at least two tertiary amino groups per molecule whose nitrogen atoms are capable of co-ordinating with M, and
   (b) dissociating the adduct to liberate the metal alkyl at a pressure P and at a temperature below the sublimation temperature or boiling point of the tertiary amine at pressure P as the case may be, characterised in that the tertiary amine has a molecular structure whose nitrogen atoms, for geometric reasons, co-ordinate with different atoms M such that the adduct formed has a vapour pressure of less than 1.33 Pa at its dissociation temperature at that pressure.

2. A method according to claim 1 characterised in that the vapour pressure of the adduct is less than 1.33 Pa at 20° C. above the dissociation temperature of the adduct at that pressure.

3. A method according to claim 2 characterised in that the vapour pressure of the adduct is less than 1.3 Pa at 30° C. above the dissociation temperature of the adduct at that pressure.

4. A method according to claim 1 characterised in that the Lewis base has a melting point in the range 5° C. to 200° C. and a boiling point at atmosphere pressure of more than 200° C.

5. A method according to claim 1 characterised in that the Lewis base is a solid at the dissociation temperature of the adduct at 1.33 Pa.

6. A method according to claim 5 characterised in that the Lewis base is a solid at least 20° C. above the dissociation temperature of the adduct at 1.33 Pa.

7. A method according to claim 1, characterized in that the Lewis base comprises a tertiary amine of general formula I

wherein each X is independently selected from tertiary amino substituent groups and Ar is an arylene bridging group, provided that the amino substituent groups X are separated by at least two arylene ring atoms on the Lewis base molecule.

8. A method according to claim 7 characterised in that the Lewis base comprises a tertiary amine of general formula II

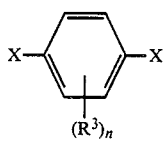

II wherein each X is as defined in claim 7, n is 0 or an integer from 1 to 4, and each $R^3$ is independently selected from $C_1$-$C_8$ alkyl.

9. A method according to claim 8 characterised in that each X is independently selected from —$NR^4R^5$ where $R^4$ and $R^5$ are independently selected from $C_1$-$C_8$ alkyl, and n is 0.

10. A method according to claim 1 characterised in that the Lewis base comprises a pyridyl compound substituted in the para- or meta- ring positions by a tertiary amino group.

11. A method according to claim 10 characterised in that the Lewis base is of general formula III $$Py^1-(B)_m-Py^2 \quad \text{III}$$

wherein $Py^1$ and $Py^2$ are independently selected from optionally-substituted pyridyl provided that at least one of $Py^1$ and $Py^2$ is either optionally-substituted 3-pyridyl or optionally-substituted 4-pyridyl, B is arylene, alkylene, or cycloalkylene, and m is 0 or 1.

12. A method according to claim 11 characterised in that m is 0 and the Lewis base is either 3,3'-bipyridyl or 4,4'-bipyridyl.

13. A method according to claim 10 characterized in that the pyridyl compound is substituted in the para-ring position by a tertiary amino group X, which is independently selected from —$NR^4R^5$ where $R^4$ is $C_1$-$C_8$ and $R^5$ is

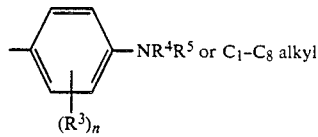

provided that the number of nitrogen atoms in each group X is from 1 to 3, n is 0 or an integer from 1 to 4, and each $R^3$ is independently selected from $C_1$-$C_8$ alkyl.

14. A method according to claim 1 characterised in that the Lewis base is an optionally-substituted pyrazine.

15. A method according to claim 14 characterized in that the Lewis base is of general formula IV

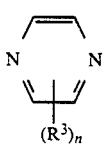

IV wherein n is 0 or an integer from 1 to 4 and each $R^3$ is independently selected from $C_1$-$C_8$ alkyl.

* * * * *